(12) United States Patent
Zaworotko et al.

(10) Patent No.: US 12,234,248 B2
(45) Date of Patent: Feb. 25, 2025

(54) CO-CRYSTAL COMPOUNDS COMPRISING LITHIUM IONS AND ISONICOTINAMIDE

(71) Applicants: UNIVERSITY OF LIMERICK, Limerick (IE); UFSCAR-FEDERAL UNIVERSITY OF SAO CARLOS, Sao Paulo (BR)

(72) Inventors: Michael Zaworotko, Limerick (IE); Miranda Perry, Limerick (IE); Renato Lajarim Carneiro, Sao Paulo (BR); Naga Duggirala, Limerick (IE); Daniel O'Nolan, Limerick (IE); Peraka Krishna, Limerick (IE)

(73) Assignees: UNIVERSITY OF LIMERICK, Limerick (IE); UFSCAR-FEDERAL UNIVERSITY OF SAO CARLOS, Sao Paulo (BR)

( * ) Notice: Subject to any disclaimer, the term of this patent is extended or adjusted under 35 U.S.C. 154(b) by 0 days.

(21) Appl. No.: 18/190,060

(22) Filed: Mar. 24, 2023

(65) Prior Publication Data
US 2023/0234972 A1    Jul. 27, 2023

Related U.S. Application Data

(62) Division of application No. 16/097,444, filed as application No. PCT/EP2017/060221 on Apr. 28, 2017, now abandoned.

(51) Int. Cl.
| C07F 1/00 | (2006.01) |
| C07D 207/16 | (2006.01) |
| C07D 213/81 | (2006.01) |

(52) U.S. Cl.
CPC ............ *C07F 1/005* (2013.01); *C07D 207/16* (2013.01); *C07D 213/81* (2013.01); *C07B 2200/13* (2013.01)

(58) Field of Classification Search
None
See application file for complete search history.

(56) References Cited

U.S. PATENT DOCUMENTS

| 9,840,521 | B2 | 12/2017 | Zaworotko et al. |
| 10,435,416 | B2 | 10/2019 | Zaworotko et al. |
| 10,870,665 | B1 | 12/2020 | Zaworotko et al. |
| 2003/0225142 | A1 | 12/2003 | Crooks et al. |
| 2008/0261101 | A1 | 10/2008 | de Figueiredo Gomes et al. |
| 2009/0209604 | A1 | 8/2009 | Zhang |
| 2014/0242193 | A1 | 8/2014 | Zaworotko et al. |

FOREIGN PATENT DOCUMENTS

| WO | 2012129568 A2 | 9/2012 |
| WO | 2012129568 A3 | 9/2012 |
| WO | 2014172650 A1 | 10/2014 |

OTHER PUBLICATIONS

Aakeröy et al., "A High-Yielding Supramolecular Reaction," J. Am. Chem. Soc., Jul. 24, 2002, 124, 14425-14432.
Báthori et al., "Pharmaceuticals Co-crystals with Isonicotinamide—Vitamin B3, Clofibric Acid, and Diclofenac—and Two Isonicotinamide Hydrates," Crystal Growth & Design Article, American Chemical Society, Dec. 20, 2010, vol. 11, pp. 75-87, downloaded via the United States Patent and Trademark Office on Jun. 9, 2022.
European Search Report for corresponding EP Application No. 16167817.2 dated Aug. 9, 2016, 8 pages.
International Preliminary Report on Patentability for corresponding International Application No. PCT/EP2017/060221 dated Oct. 30, 2018, 8 pages.
International Search Report and Written Opinion for corresponding International Application No. PCT/EP2017/060221 dated Jun. 1, 2017, 15 pages.
Smith et al., "Improving Lithium Therapeutics by Crystal Engineering of Novel Ionic Cocrystals," Molecular Pharmaceutics Article, American Chemical Society, published Nov. 5, 2013, pp. 4728-4738.
Yeung et al., "Ligand-Directed Control over Crystal Structures of Inorganic-Organic Frameworks and Formation of Solid Solutions," Angewandte Communications, Angew. Chem. Int. Ed., published online Mar. 26, 2013, 52, pp. 5544-5547.

*Primary Examiner* — Katherine Peebles
(74) *Attorney, Agent, or Firm* — Hoffman Warnick LLC

(57) ABSTRACT

Stable crystal forms comprising lithium ions and the conjugate base of an organic acid which is in the form of anhydrous coordination polymer that exhibit improved in vivo performance with respect to lithium carbonate.

5 Claims, 9 Drawing Sheets

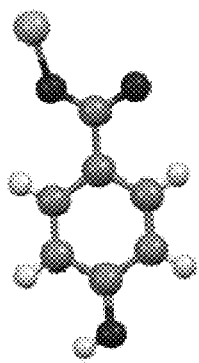
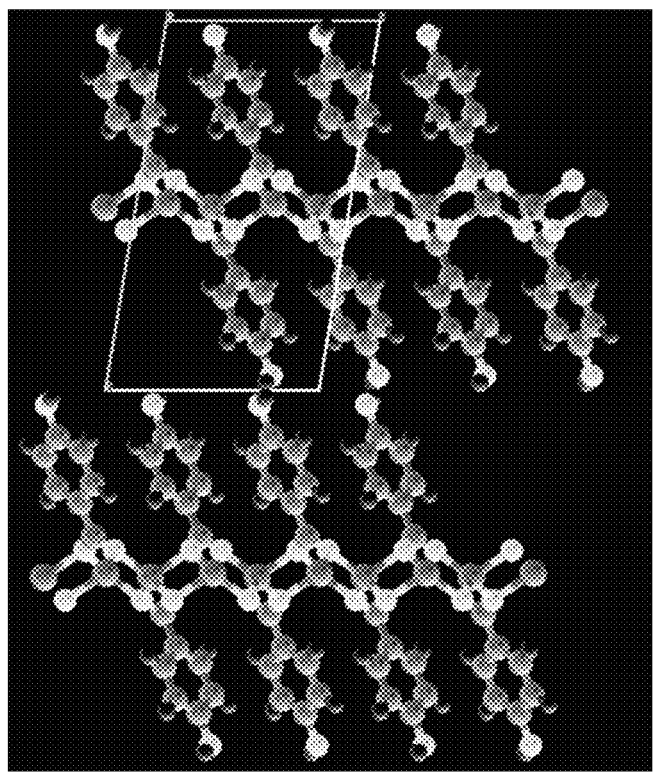
Fig. 4A                    Fig. 4B
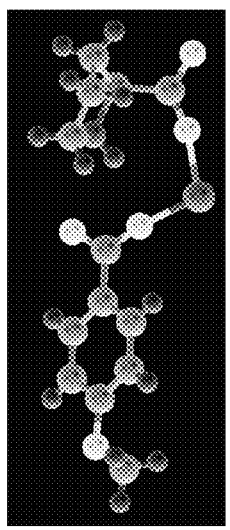
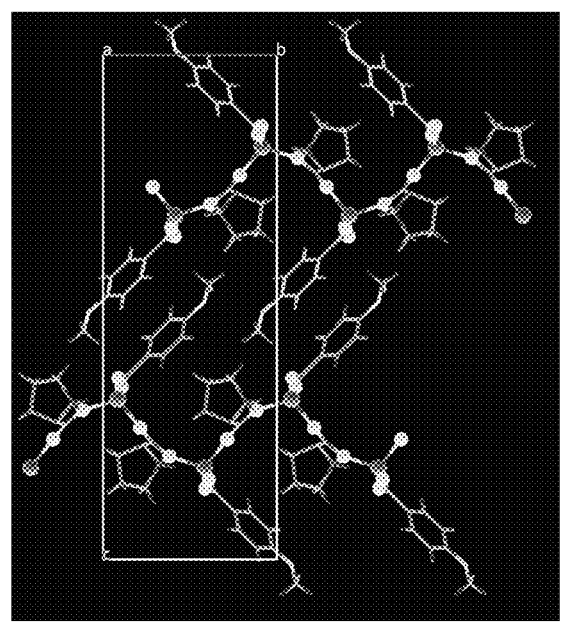
Fig. 5A                    Fig. 5B

CO-CRYSTAL COMPOUNDS COMPRISING LITHIUM IONS AND ISONICOTINAMIDE

The present invention relates to pharmaceutical compositions comprising lithium salts and methods and uses relating thereto. In particular, the invention relates to stable solid forms of lithium which have improved biological performance, in particular stable crystalline forms.

Lithium compounds are used as a psychiatric medication for the treatment of depressive diseases, for example major depressive disorder and bipolar disorder.

The most commonly used medications currently used to treat depressive diseases are selective serotonin re-uptake inhibitors (SSRIs). However, these drugs carry a risk of increased suicidality in some patients.

Lithium has much lower risk of suicidality. However current lithium treatments have significant side effects, including lithium toxicity, caused by a poorly suited pharmacokinetic profile. With current treatments, lithium concentrations in the blood peak sharply within a few hours, leading to high toxicity. The risk of toxicity means that blood monitoring is essential. This, along with other unpleasant side effects such as increased thirst, increased urination and shakiness, reduce compliance and many patients find lithium therapy intolerable.

Lithium is currently provided as a drug substance in the form of lithium carbonate or lithium citrate. However, these compounds have a narrow therapeutic window. It would be desirable to find an alternative therapeutic source of lithium having reduced toxicity and fewer side effects.

The site of action for lithium is in the brain and thus the drug needs to cross the blood-brain barrier. The low brain bioavailability of current treatments means that high doses are often needed, leading to toxicity problems and a narrow therapeutic window. The provision of a drug substance that represents an alternative source of lithium may affect the rate at which lithium enters the brain and/or the mechanism by which it crosses the blood-brain barrier. This could provide an improved therapeutic window.

When formulating pharmaceutical preparations the stability of the active ingredients is essential. Many drug substances deteriorate during distribution and storage especially in hot and humid conditions. Any drug substance to be used in pharmaceutical preparation must be air and moisture stable. Maintaining the crystal form of the drug substance is also of importance as the crystal form can influence the physicochemical properties, for example solubility, melting point and hygroscopicity.

Unfortunately, many lithium containing compounds are hygroscopic. There have been attempts to provide lithium compositions having improved hygroscopicity. However, this has been with little success until now.

WO 2014/172650 describes the preparation of organic anion lithium ionic cocrystal compounds comprising an organic acid and a neutral organic molecule. Various cocrystals, cocrystals solvates and cocrystals hydrates are described. However, the stability of these compounds is not discussed.

The present inventors have surprisingly found that certain crystalline forms of organic acid salts of lithium have significantly improved stability compared with other forms. Thus, such species may be suitable for inclusion in pharmaceutical preparations.

Furthermore, the present inventors have prepared novel compounds comprising lithium that have good brain bioavailability, and in particular show improved in vivo characteristics compared with lithium carbonate.

BRIEF DESCRIPTION OF THE DRAWINGS

FIGS. 4A and 4B show the asymmetric unit and crystal packing of the material prepared in Example 4, respectively, according to embodiments of the present disclosure;

FIGS. 5A and 5B show the asymmetric unit and crystal packing of the material prepared in Example 5, respectively, according to embodiments of the present disclosure;

Figure 1A:
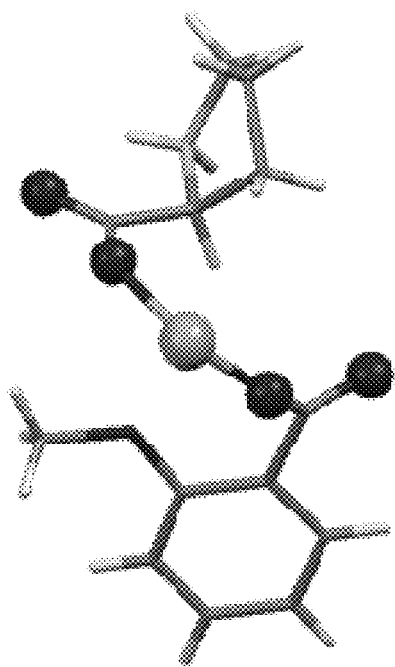
FIGS. 1A and 1B show the asymmetric unit and crystal packing of the material prepared in Example 1, respectively, according to embodiments of the present disclosure.

According to a first aspect of the present invention, there is provided a stable crystal form comprising lithium ions and the conjugate base of an organic acid which is in the form of an anhydrous coordination polymer.

The present invention relates to crystal forms comprising lithium and the conjugate base of an organic acid. By crystal form we mean to refer to a material which has a repeating arrangement of ions and optionally molecules in 3 dimensions.

Unless otherwise stated when terms of art are used in this specification, we mean to refer to the common general usage of the term.

Stable crystal forms of the present invention are in the form of an anhydrous coordination polymer. By anhydrous we mean that there are no water molecules present in the crystal forms of the present invention. Thus, there are no water molecules present in either a bound form (e.g. as an aqua complex) or an unbound form (e.g. as a stoichiometric or non-stoichiometric hydrated crystal structure).

The crystal forms of the present invention are coordination polymers. As the skilled person will appreciate a coordination polymer is a type of network solid with repeating coordination entities extending in 1, 2 or 3 dimensions. The coordination polymers of the present invention contain lithium cationic centres linked by organic ligands. Thus, the crystal forms of the present invention are not formed of discrete molecules or ions but comprise an extended structure in the form of a polymer, with repeating units.

Preferably the coordination polymer of the present invention includes repeating units in at least two dimensions.

The crystal forms of the present invention comprise lithium cations and the conjugate base of the organic acid will be present as an anion. In some embodiments the crystal forms of the present invention further include one or more additional molecules or ions, as further described herein.

The crystal forms of the present invention typically include one or more repeating units, which are linked to form the coordination polymer.

The repeating unit of the coordination polymer preferably may contain one or more lithium ions. Suitably each repeating unit contains one or two lithium ions.

The crystal forms of the present invention comprise the conjugate base of an organic acid. The organic acid may be a carboxylic acid or a sulfonic acid. Preferably the organic acid is a carboxylic acid. Suitable carboxylic acids include monocarboxylic acids, dicarboxylic acids and polycarboxylic acids. The conjugate base of an organic acid RCOOH is the carboxylate residue RCOO$^-$. The conjugate base of a monocarboxylic acid includes a single carboxylate group COO$^-$, the conjugate base of a dicarboxylic acid includes two carboxylate groups COO$^-$, etc.

In the crystal forms of the present invention, each repeating unit of the coordination polymer suitably includes one lithium ion per carboxylate residue COO$^-$. Thus, salts of dicarboxylic acids will include two lithium ions etc.

Dicarboxylic acid anions are particularly advantageous as the inclusion of two lithium ions per repeat unit means that there may be higher relative lithium content per gram of material.

In some embodiments the repeating unit of the coordination polymer may include the conjugate base of a single organic acid molecule or the conjugate base of two or more organic acid molecules. When the repeating unit comprises the conjugate base of more than one organic acid molecule, each may be the residue of the same or a different organic acid.

In embodiments in which the conjugate base of more than one organic acid molecule is included in each repeating unit these are preferably the same as each other.

In some embodiments the unit cell of the crystal form may include two or more units of the same acid in different orientations within the crystal, i.e. the acid units are in distinct crystallographic environments.

Suitable organic acids for inclusion in the crystal forms of the present invention include p-toluenesulfonic acid, malic acid, maleic acid, lactic acid, camphorsulfonic acid, salicylic acid, oxalic acid, fumaric acid, cinnamic acid, citric acid, methane sulfonic acid, succinic acid, benzoic acid, hydroxybenzoic acids and methoxybenzoic acids.

In preferred embodiments the organic acid is a carboxylic acid. Preferably the carboxylic acid is selected from aromatic carboxylic acids and/or dicarboxylic acids.

Suitably when the carboxylic acid is an aromatic carboxylic acid this is preferably an optionally substituted benzoic acid. Preferred aromatic acids include benzoic acid, hydroxy substituted benzoic acids and alkoxy, especially methoxy, substituted benzoic acids.

Suitable dicarboxylic acids include maleic acid, benzene dicarboxylic acids, fumaric acid, succinic acid, maleic acid, oxalic acid and citric acid.

Preferred dicarboxylic acids include fumaric acid, succinic acid and oxalic acid. Especially preferred dicarboxylic acids are fumaric acid and succinic acid.

In some preferred embodiments the crystal forms of the present invention comprise lithium ions and the conjugate base of one or more acids selected from dicarboxylic acids and aromatic carboxylic acids.

The crystal forms of the present invention preferably comprise lithium ions and the conjugate base of one or more acids selected from dicarboxylic acids and optionally substituted benzoic acids.

Suitably the crystal forms of the present invention comprise lithium ions and the conjugate base of one or more acids selected from fumaric acid, succinic acid, oxalic acid, benzoic acid, 2-methoxybenzoic acid, 3-methoxybenzoic acid, 4-methoxybenzoic acid, 4-hydroxybenzoic acid and salicylic acid.

In some preferred embodiments the organic acid is not salicylic acid or benzoic acid.

Suitably the present invention provides a stable crystal form comprising lithium ions and the conjugate base of an organic acid which is in the form of an anhydrous coordination polymer wherein the organic acid is not salicylic acid or benzoic acid.

Suitably the present invention provides a stable crystal form comprising lithium ions and the conjugate base of an organic acid which is in the form of anhydrous coordination polymer wherein the organic acid is selected from dicarboxylic acids and aromatic carboxylic acids other than salicylic acid or benzoic acid.

Suitably the crystal forms of the present invention comprise lithium ions and the conjugate base of one or more acids selected from fumaric acid, succinic acid, oxalic acid, 2-methoxybenzoic acid, 3-methoxybenzoic acid, 4-methoxybenzoic acid and 4-hydroxybenzoic acid.

In especially preferred embodiments the crystal forms of the present invention comprise lithium ions and the conjugate base of one or more acids selected from fumaric acid, succinic acid and a methoxy-substituted benzoic acid.

In especially preferred embodiments the crystal forms of the present invention comprise lithium ions and the conjugate base of one or more acids selected from fumaric acid, succinic acid and 4-methoxybenzoic acid.

In some embodiments the crystal forms of the present invention may include one or more further molecules or ions. These are suitably pharmaceutically acceptable compounds. These are suitably molecules or ions that are incorporated into and form part of the crystal form. Preferably the one or more additional molecules or ions are charge-neutral overall. Thus, in some embodiments the crystal form may further comprise an additional cation and an additional anion with balanced charges. In some embodiments the crystal form may comprise an additional zwitterionic molecule. In some embodiments the crystal form includes an additional neutral molecule.

Preferably the one or more additional molecules and/or ions present in the crystal form is an electron pair donor. Suitable additional molecules/ions that may be incorporated in the crystal form include amino acids, vitamins such as nicotinamide, sugars, flavonoids, isonicotinamide, imidazole, urea, 4-hydroxyproline, sarcosine, oxalic acid and lactic acid.

Preferred additional molecules that may be incorporated in the crystal forms of the present invention include amino acids and amides.

Especially preferred additional molecules include nicotinamide, isonicotinamide, L-proline and 4-hydroxyproline.

Suitably the additional molecule is selected from isonicotinamide and L-proline.

In some embodiments the stable crystal forms of the present invention comprise lithium ions, the conjugate base of an organic acid and an additional neutral molecule wherein the organic acid is not salicylic acid or benzoic acid.

In some embodiments the stable crystal forms of the present invention comprise lithium ions and the conjugate base of one or more organic acids selected from dicarboxylic acids and aromatic carboxylic acids, and an additional neutral molecule.

In some embodiments the stable crystal forms of the present invention comprise lithium ions; the conjugate base of one or more organic acids selected from fumaric acid, succinic acid and a methoxy-substituted benzoic acid; and an additional molecule selected from amino acids, nicotinamide, isonicotinamide, imidazole, urea, 4-hydroxyproline, sarcosine, oxalic acid and lactic acid.

In some embodiments the stable crystal forms of the present invention comprise lithium ions; the conjugate base of one or more organic acids selected from fumaric acid, succinic acid, oxalic acid, 2-methoxybenzoic acid, 3-methoxybenzoic acid, 4-methoxybenzoic acid and 4-hydroxybenzoic acid; and an additional molecule selected from nicotinamide, isonicotinamide and L-proline.

In some embodiments the stable crystal forms of the present invention comprise lithium ions; the conjugate base of one or more organic acids selected from fumaric acid, succinic acid and 4-methoxybenzoic acid; and an additional molecule selected from nicotinamide isonicotinamide and L-proline.

The crystal forms of the present invention are coordination polymers. The crystal forms include lithium ions and one or more ligands. At least one ligand is the conjugate base of an organic acid. Further ligands include neutral molecules. At least one type of ligand in each crystal form is coordinated to at least two different lithium ions.

In one embodiment the stable crystal form of the present invention comprises lithium cations, fumarate anions and isonicotinamide molecules, suitably in a molar ratio of 2:1:2.

In one embodiment the stable crystal form of the present invention comprises lithium cations, succinate anions and isonicotinamide molecules, suitably in molar ratio of 2:1:2.

In one embodiment the stable crystal form of the present invention comprises lithium cations, 4-methoxybenzoate anions and L-proline molecules, suitably in a molar ratio of 1:1:1.

In one embodiment the stable crystal form of the present invention comprises lithium cations, 2-methoxybenzoate anions and L-proline molecules, suitably in a molar ratio of 1:1:1.

In one embodiment the stable crystal form of the present invention comprises lithium cations, 3-methoxybenzoate anions and L-proline molecules, suitably in a molar ratio of 1:1:1.

In one embodiment the stable crystal form of the present invention comprises lithium cations, benzoate anions and L-proline molecules, suitably in a molar ratio of 1:1:1.

In one embodiment the stable crystal form of the present invention comprises lithium cations, salicylate anions and 4-hydroxyproline molecules, suitably in a molar ratio of 1:1:1.

In one embodiment the stable crystal form of the present invention comprises lithium cations, salicylate anions and L-proline molecules, suitably in a molar ratio of 1:1:1.

In one embodiment the stable crystal form of the present invention comprises lithium cations and 4-hydroxybenzoate anions, suitably in a molar ratio of 1:1.

In one embodiment the stable crystal form of the present invention comprises lithium cations and 4-methoxybenzoate anions, suitably in a molar ratio of 1:1.

In one embodiment the stable crystal form of the present invention comprises lithium cations and fumarate anions, suitably in a molar ratio of 2:1.

In one embodiment the stable crystal form of the present invention comprises lithium cations and succinate anions, suitably in a molar ratio of 2:1.

In one embodiment the stable crystal form of the present invention comprises lithium cations and oxalate anions, suitably in a molar ratio of 2:1.

In one embodiment the stable crystal form of the present invention comprises lithium cations and benzoate anions, suitably in a molar ratio of 1:1.

In especially preferred embodiments the crystal forms of the present invention comprise lithium ions and the conjugate base of one or more acids selected from fumaric acid, succinic acid and 4-methoxybenzoic acid and a further molecule selected from isonicotinamide and L-proline.

Preferably the crystal form of the present invention is selected from:
(a) an anhydrous coordination polymer comprising lithium cations, fumarate anions and isonicotinamide molecules, suitably in a molar ratio of 2:1:2;
(b) an anhydrous coordination polymer comprising lithium cations, succinate anions and isonicotinamide molecules, suitably in molar ratio of 2:1:2; and
(c) an anhydrous coordination polymer comprising lithium cations, 4-methoxybenzoate anions and L-proline molecules, suitably in a molar ratio of 1:1:1.

The crystal forms of the present invention are in the form of coordination polymers rather than discrete molecular complexes or complex ions. The crystal forms are not hydrates or aqua complexes: they are anhydrous.

It was highly unexpected that anhydrous materials would exhibit such high stability in hot and humid conditions.

The present inventors have surprisingly found that lithium salts of organic acids which are in the form of anhydrous coordination polymers are in general much more stable to stresses such as humidity and heat than salts which are in the form of molecular complexes or which include one or more water molecules in the crystal forms (i.e. hydrates or aqua complexes).

The present invention relates to stable crystal forms. The stable crystal forms of the present invention are suitably stable in the presence of air and water. As such they are suitably for use in drug products.

The crystal forms of the present invention are suitably not deliquescent.

Suitably they are not hygroscopic. Suitably the crystal forms of the present invention do not degrade under standard atmospheric conditions upon storage for up to 24 hours.

Preferably the crystal forms of the present invention do not degrade under standard atmospheric conditions upon storage for up to one week, preferably up to one month, more preferably up to three months, most preferably up to six months.

It is essential that pharmaceutical compositions are stable under the warm humid conditions commonly found in tropical climates around the world. The crystal forms of the present invention are stable under such conditions. It is unexpected and surprising that anhydrous polymers have been found to have excellent stability in humid conditions.

Preferably the crystal forms of the present invention do not degrade on exposure to an atmosphere of 75% relative humidity at a temperature of 40° C. after a period of one week, preferably after a period of one month, suitably after a period of two months, for example after a period of six months.

By does not degrade it is meant that the crystal form suitably does not noticeably (i.e. to the naked eye) change in appearance. Suitably it does not change colour. Suitably it retains a crystalline appearance. Suitably the crystal form does not decrease in weight. Preferably it increases in weight by less than 10% during the specified period, preferably by less than 5%, more preferably by less than 2%, preferably less than 1%, more preferably less than 0.1%.

Suitably a crystal form which does not degrade retains its crystalline integrity. The crystal form suitably remains substantially identical and no water or other molecules are incorporated into the crystal form. Suitably the weight of the crystal forms does not change.

Suitably the powder X-ray diffraction (PXRD) pattern of a crystal form that is stable does not significantly change over the specified period. Suitably peak positions in the PXRD pattern do not vary by more than 0.2° in 2theta.

Preferably after storage in an atmosphere of 75% relative humidity at a temperature of 40° C. for a period six months the crystal form of the invention increases in weight by less than 1%, preferably less than 0.1%, and preferably the peak positions in the PXRD pattern do not vary by more than 0.2° in 2theta during this period.

According to a second aspect of the present invention there is provided a method of preparing a crystal form of the first aspect, the method comprising admixing a source of lithium ions and an organic acid in the presence of a solvent and allowing the solvent to evaporate.

In some embodiments in which the crystal form further includes one or more neutral molecules the method of the second aspect suitably involves admixing the one or more neutral molecules with the source of lithium ions and the organic acid in the presence of a solvent.

A preferred source of lithium ions is lithium hydroxide.

The lithium hydroxide is suitably added in an approximately 1:1 molar equivalent per mole of protons provided by the acid.

Suitable solvents for use in preparing the stable crystal forms of the invention include water, acetic acid, acetone, acetonitrile, anisole, 1-butanol, 2-butanol, butyl acetate, tert-butylmethyl ether, chloroform, dimethylformamide, dimethylsulfoxide, 1,4-dioxane, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, methanol, 1-propanol, 2-propanol, propyl acetate, tetrahydrofuran and toluene.

In preferred embodiments the solvent is water, ethanol or a mixture thereof.

The method of the second aspect involves administering the source of lithium ions and the organic acid in the presence of a solvent. In same embodiments the source of lithium ions and the organic acids are dissolved in the solvent.

In some embodiments the reaction mixture may be heated to aid dissolution. In some embodiments the reaction mixture may be stirred. In some embodiments the reaction mixture may be sonicated. The time for which the mixture is heated, stirred or sonicated may be adjusted as appropriate and the selection of suitable conditions and reaction times is within the competence of the skilled person.

In some embodiments the source of lithium ions and the organic acid may be ground together in the presence of a very small amount of solvent in a process known as solvent-drop grinding or liquid-assisted grinding. Such methods are known to the person skilled in the art.

The crystal forms of the present invention are particularly suitable for use in pharmaceutical preparations, especially for the treatment of a depressive disease.

According to a third aspect of the present invention there is provided a pharmaceutical composition comprising a crystal form of the first aspect.

The pharmaceutical composition may be any suitable form. Preferably it is in the form of a solid, for example a powder, capsule, tablet or lozenge. It may suitably be provided in unit dose form, for example in a sachet. It may also be provided in semisolid form or as an emulsion or suspension.

The pharmaceutical composition of the third aspect may consist essentially of the crystal form of the first aspect or may contain one or more other additional ingredients. Suitably the composition may include a pharmaceutically acceptable carrier. Examples of suitable pharmaceutically acceptable carriers will be known to the person skilled in the art.

The composition may further comprise one or more additional pharmaceutically acceptable excipients, such as fillers, binders, lubricants, flavours, preservatives, colourings, disintegrants, suspending agents, stabilizing agents and coatings. Examples of such components are known to the person skilled in the art.

According to a fourth aspect of the present invention there is provided a method of preparing a pharmaceutical composition of the third aspect, the method comprising preparing a crystal form according to the method of the second aspect and optionally admixing the crystal form with one or more additional pharmaceutically acceptable ingredients.

The present invention may suitably provide a method of providing a storage stable pharmaceutical preparation comprising lithium, the method comprising selecting a stable crystal form comprising lithium ions and the conjugate base of an organic acid which is in the form of anhydrous coordination polymer and admixing said crystal form with one or more pharmaceutically acceptable ingredients.

Suitably the present invention provides the use of a stable crystal form of the first aspect in the preparation of a storage stable pharmaceutical preparation.

Suitable additional pharmaceutically acceptable ingredients include carriers and other excipients. Suitable such ingredients are known to the person skilled in the art.

The present invention relates in particular to the use of crystal forms. However, pharmaceutical compositions may be prepared using amorphous forms of these materials.

According to a fifth aspect of the present invention there is provided a stable crystal form of the first aspect for use in therapy.

Suitably the fifth aspect provides a stable crystal form of the first aspect for use in the treatment of a depressive disease.

The invention may suitably provide a pharmaceutical composition comprising a crystal form of the first aspect for use in the treatment of a depressive disease.

According to a sixth aspect of the present invention there is provided a method of treating a mental illness, the method comprising administering to a patient a pharmaceutical composition of the third aspect.

The mental illness may be selected from bipolar disorder, bipolar depression, depression, schizophrenia, eating disorders (anorexia and bulimia) and headache and aggressive behaviour in people with attention deficit hyperactivity disorder.

Suitably the mental illness is a depressive disease.

Preferably the depressive disease is major depressive disorder or bipolar disorder.

Preferably the depressive disease is bipolar disease.

Surprisingly the in vivo performance of the crystal forms of the present invention has been found to be highly advantageous. In particular, the crystal forms of the invention have been found to exhibit a lower maximum concentration in blood plasma ($C_{max}$) and a later time of maximum concentration in the brain ($T_{max}$) after a single oral dose compared with an equivalent single oral dose of lithium carbonate.

This is highly advantageous and unexpected and is associated with lower toxicity and the possibility of less frequent administration and/or lower dosages. Less frequent administration is associated with improved compliance.

The crystal forms of the present invention have been found to provide a lower maximum concentration of lithium in the blood compared with when the same amount of lithium is administered as lithium carbonate. This may help reduce the toxicity of a pharmaceutical composition.

Thus, the present invention may suitably provide a pharmaceutical composition of the third aspect having lower toxicity than lithium carbonate.

The maximum concentration of lithium in the brain has been found to occur later when using the stable crystal form of the invention compared with when the same amount of lithium is administered as lithium carbonate. This may mean that a pharmaceutical composition has an improved efficacy, can be used at a lower dosage and/or can be administered less frequently.

Thus, the present invention may suitably provide a pharmaceutical composition of the third aspect having improved efficacy.

The present invention may provide the use of a stable crystal form comprising lithium ions and the conjugate base of an organic acid which is in the form of an anhydrous coordination polymer to provide an alternative therapeutic treatment to lithium carbonate.

Treatment with the crystal form of the present invention compared with treatment with lithium carbonate may provide one or more advantages. These are suitably selected from:
  an enhanced therapeutic effect for a given dose of lithium;
  a reduction in toxicity;
  a reduced dose to achieve the same therapeutic effect;
  less frequent administration; and
  improved compliance.

A number of materials of the present invention have been found to have particularly advantageous in vivo properties. These novel materials are stable solids whether in crystalline or amorphous form.

According to a seventh aspect of the present invention there is provided a compound comprising lithium ions, the conjugate base of one or more acids selected from fumaric acid, succinic acid and 4-methoxybenzoic acid and a further molecule selected from isonicotinamide and L-proline.

Preferably the compound of the seventh aspect is selected from:
  (a) a compound comprising lithium cations, fumarate anions and isonicotinamide molecules, suitably in a molar ratio of 2:1:2;
  (b) a compound comprising lithium cations, succinate anions and isonicotinamide molecules, suitably in molar ratio of 2:1:2; and
  (c) a compound comprising lithium cations, 4-methoxybenzoate anions and L-proline molecules, suitably in a molar ratio of 1:1:1.

In some embodiments the present invention provides a compound comprising lithium cations, fumarate anions and isonicotinamide molecules, suitably in a molar ratio of 2:1:2.

In some embodiments the present invention provides a compound comprising lithium cations, succinate anions and isonicotinamide molecules, suitably in molar ratio of 2:1:2.

In some embodiments the present invention provides a compound comprising lithium cations, 4-methoxybenzoate anions and L-proline molecules, suitably in a molar ratio of 1:1:1.

The compound of the seventh aspect of the present invention preferably has a formula selected from $[Li_2(fumarate)(isonicotinamide)_2]_n$, $[Li(4-methoxybenzoate)(L-proline)]_n$, and $[Li_6(succinate)_3(isonicotinamide)_6]_n$.

The compound of the seventh aspect includes lithium ions, the conjugate base of an organic acid and a neutral molecule. The components of the compound are suitably linked by coordination bonds.

The compounds of the seventh aspect of the present invention are suitably network solids. Preferably the compounds of the seventh aspect are coordination polymers.

Preferably the compounds of the present invention are anhydrous materials. Preferably they are anhydrous coordination polymers.

Most preferably the compounds of the seventh aspect are provided in a stable crystalline form as anhydrous coordination polymers. Suitably the compounds of the seventh aspect are stable crystal forms falling within the first aspect of the present invention. Suitably the compounds of the seventh aspect are prepared according to the method of the second aspect.

According to an eighth aspect of the present invention there is provided a pharmaceutical composition comprising a compound of the seventh aspect.

The pharmaceutical composition may be any suitable form. Preferably it is in the form of a solid, for example a powder, capsule, tablet or lozenge. It may suitably be provided in unit dose form, for example in a sachet. It may also be provided in semisolid form or as an emulsion or suspension.

The pharmaceutical composition of the eighth aspect may consist essentially of the compound of the seventh aspect or may contain one or more other additional ingredients. Suitably the composition may include a pharmaceutically acceptable carrier. Examples of suitable pharmaceutically acceptable carriers will be known to the person skilled in the art.

The composition may further comprise one or more additional pharmaceutically acceptable excipients, such as fillers, binders, lubricants, flavours, preservatives, colourings, disintegrants, suspending agents, stabilizing agents and coatings. Examples of such components are known to the person skilled in the art.

According to a ninth aspect of the present invention there is provided a method of preparing a pharmaceutical composition of the eighth aspect, the method comprising admixing a compound of the seventh aspect with one or more additional pharmaceutically acceptable ingredients.

In the ninth aspect the compound of the seventh aspect may be included in the composition in amorphous or crystalline form. In some embodiments the compound may be prepared as a crystalline solid, ground into amorphous form and then admixed with one or more additional pharmaceutically acceptable ingredients. In some embodiments the compound may be provided in crystalline form and directly admixed with one or more additional pharmaceutically acceptable ingredients.

According to a tenth aspect of the present invention there is provided a compound comprising lithium ions, the conjugate base of one or more acids selected from fumaric acid, succinic acid and 4-methoxybenzoic acid and a further molecule selected from isonicotinamide and L-proline for use in therapy.

Preferred features of the tenth aspect are as defined in the seventh aspect.

Suitably the tenth aspect provides a compound of the seventh aspect for use in the treatment of a depressive disease.

According to an eleventh aspect of the present invention there is provided a method of treating a mental illness, the method comprising administering to a patient a pharmaceutical composition of the eighth aspect.

The mental illness may be selected from biopolar disorder, bipolar depression, depression, schizophrenia, eating disorders (anorexia and bulimia) and headache and aggressive behaviour in people with attention deficit hyperactivity disorder.

Suitably the mental illness is a depressive disease.

Preferably the depressive disease of the tenth or eleventh aspect is major depressive disorder or bipolar disorder.

Preferably the depressive disease is bipolar disease.

Surprisingly the in vivo performance of the compounds of the seventh aspect of the present invention has been found to be highly advantageous. As mentioned above and further described in the examples, crystal forms of these compounds in particular have been found to exhibit a lower maximum concentration in blood plasma ($C_{max}$) and a later time of maximum concentration in the brain ($T_{max}$) after a single oral dose compared with an equivalent single oral dose of lithium carbonate. These offers considerable advantages as is further set out above and below.

For example compared with treatment with lithium carbonate one or more advantages may be provided, for example:
an enhanced therapeutic effect for a given dose of lithium;
a reduction in toxicity;
a reduced dose to achieve the same therapeutic effect;
less frequent administration; and
improved compliance.

Any feature of any embodiment of the invention may be combined with any other feature as appropriate.

The invention will now be further described with reference to the following non-limited examples.

In the examples crystal structures were determined from data collected using a Bruker D8 Quest Diffractometer Photon 100 CMOS Detector and either a sealed Mo K$_{□1}$ tube or Cu K$_{□1}$ micro focus tube.

EXAMPLE 1—PREPARATION OF {[LI(2-METHOXYBENZOATE)(L-PROLINE)]}$_N$ (1)

50.0 mg (0.631 mmol) of lithium 2-methoxy benzoate and 45.0 mg (0.391 mmol) of L-proline were added to ca. 1.0 mL of water. The solution was then left to slowly evaporate until 5 mg crystals emerged.

The material is an anhydrous coordination polymer. Each lithium cation is tetrahedrally coordinated to oxygen and bridged by four carboxylate moieties (from two L-proline molecules and two 2-methoxybenzoate anions) forming a square grid network.

Figure 1B:
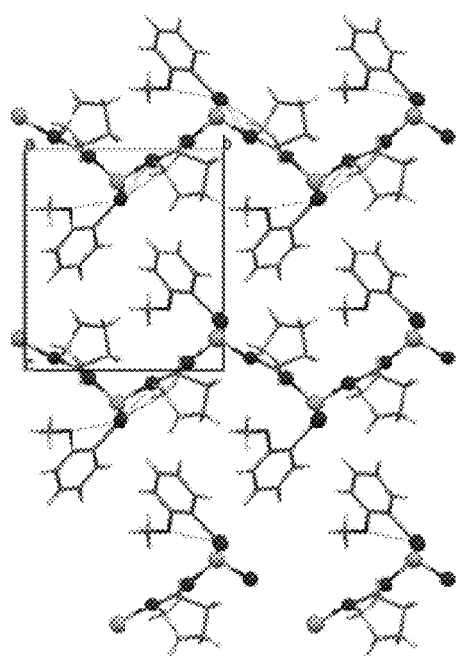

The asymmetric unit and crystal packing can be seen in FIGS. 1A and 1B.

EXAMPLE 2—PREPARATION OF [LI$_2$(FUMARATE)(ISONICOTINAMIDE)$_2$]$_N$(2)

Method 1: Single crystals: 203 mg (1.59 mmol) of lithium fumarate (previously synthesized from grinding 415 mg (17.33 mmol) of lithium hydroxide with $1.01 \times 10^3$ mg (8.66 mmol) fumaric acid with 900 microL of water by hand for ~10 min.) and 190 mg of isonicotinamide were dissolved in ca. 2 mL of 80° C. water. The solution was kept at 80° C. in a sealed vial without stirring for approximately 1 hour. After ca. 1 hour the vial was removed from the 80° C. water bath and allowed to cool. After ~1 day the lid was removed from the vial and the water was allowed to evaporate. Within five days small crystals began to form. Larger crystals grew within 20 days.

Method 2: Grinding: 96.0 mg (4.01 mmol) of lithium hydroxide, 233 mg (2.01 mmol) of fumaric acid and 489 mg (4.01 mmol) of isonicotinamde were ground together with ca. 1 mL of DI H2O. The wet mass was ground in a mortar and pestle until dry. To facilitate drying of the solid, the mortar was placed on a warm hotplate until the solid was almost dry.

Figure 2:
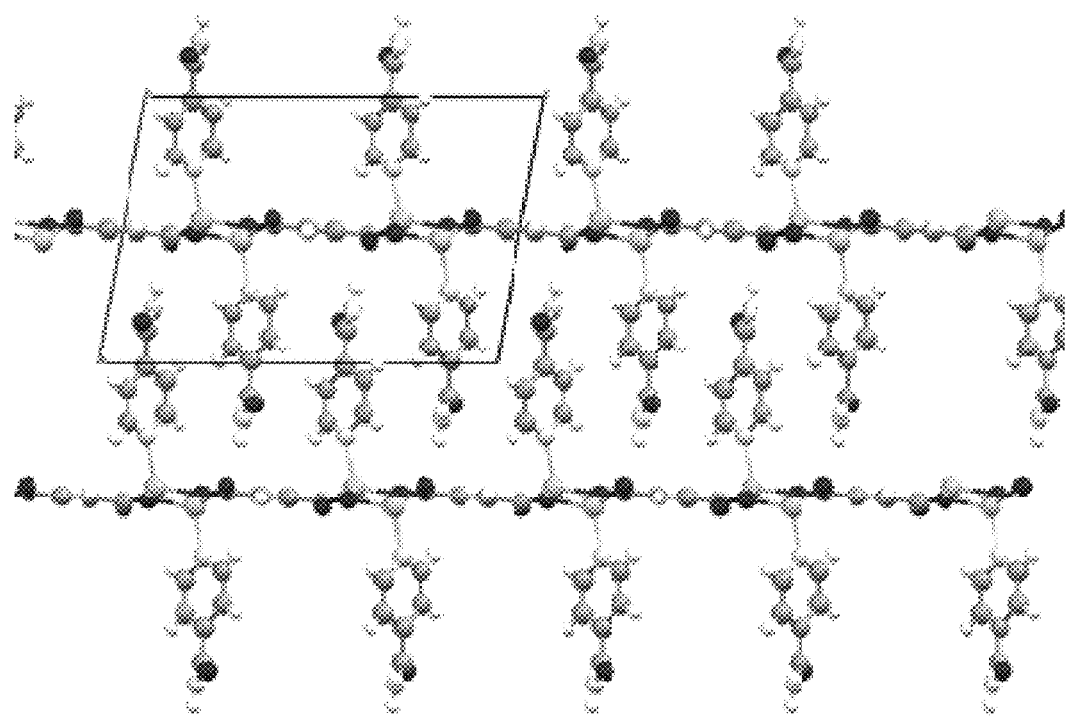
FIG. 2 shows the crystal form of the material prepared in Example 2, according to embodiments of the present disclosure.

The crystal form (FIG. 2) is a 2D coordination polymer with 4-methoxybenzoate anions coordinating to lithium cations. The material is an anhydrous coordination polymer.

EXAMPLE 3—PREPARATION OF {[LI(4-METHOXYBENZOATE)]}$_N$ (3)

Lithium hydroxide (34.6 mg, 1.44 mmol) and 4-methoxybenzoic acid (100 mg, 0.657 mmol) were dissolved in 1 mL of deionised water. The solution was left on a hot plate at ca. 45° C. for ca. 1 h. After ca. 1 h the solution was left to slowly evaporate a room temperature. After one day colourless plate-like crystals were obtained.

The molecules crystallize as a 2D coordinate polymer with the 4-methoxybenzoates coordinating to lithiums. Lithium coordinates to four oxygen atoms forming a sheet of lithium 4-methoxybenzoates. The 4-methoxybenzoates are extended above and below the lithium-oxygen interactions, generating a bilayer like structure.

Figure 3A:
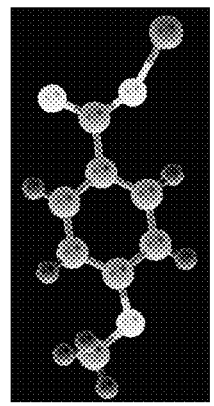
FIGS. 3A and 3B show the asymmetric unit and crystal packing of the material prepared in Example 3, respectively, according to embodiments of the present disclosure.
Figure 3B:
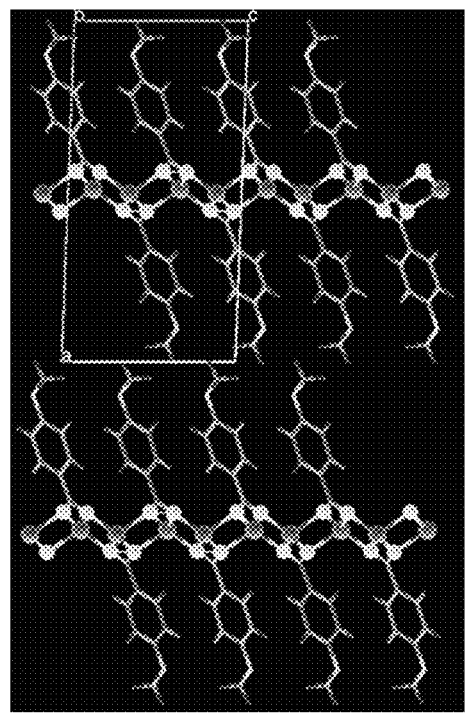

The material is an anhydrous coordination polymer and the asymmetric unit and crystal packing are shown in FIGS. 3A and 3B.

EXAMPLE 4—PREPARATION OF {[LI(4-HYDROXYBENZOATE)]}$_N$ (4)

Lithium hydroxide (34.6 mg, 1.44 mmol) and 4-hydroxybenzoic acid (100 mg, 0.724 mmol) were dissolved in ca. 1 mL of deionised water. The solution was left on a hot plate at ca. 45° C. for ca. 1 h. After 1 h the solution was left to slowly evaporate a room temperature. After one day colourless plate-like crystals were obtained.

Lithium cations and 4-hydroxybenzoate anions crystallize as a 2D coordinate polymer, packing as sheets of 4-hydroxybenzoate coordinated to lithium. Lithium coordinates to four oxygens from various carboxylates. The coordinated lithium-oxygen moieties form a sheet sustained by three different ring motifs containing either 4, 6 or 8 atoms, respectively.

The material is an anhydrous coordination polymer and the asymmetric unit and crystal packing are shown in FIGS. 4A and 4B.

EXAMPLE 5—PREPARATION OF [LI(4-METHOXYBENZOATE)(L-PROLINE)]$_N$ (5)

100 mg (0.632 mmol) of lithium 4-methoxybenzoate and 72.0 mg (0.625 mmol) of L-proline were dissolved in ca. 1 mL of water. The solution was left stirring at 45° C. for 3 days until single crystals emerged.

Each lithium cation is tetrahedrally coordinated and bridged by four carboxylate moieties (from two L-prolines and two 4-methoxybenzoate anions) to form square grid networks.

The crystal exists as anhydrous coordination polymer and the asymmetric unit and crystal packing are shown in FIGS. 5A and 5B.

EXAMPLE 6—PREPARATION OF [LI(3-METHOXYBENZOATE)(L-PROLINE)]$_N$ (6)

L-proline (72.8 mg, 0.632 mmol) and lithium 3-methoxybenzoate (100 mg, 0.632 mmol) were dissolved in ca. 1 mL of deionised water. The solution was left for ca. 1 h on a hot plate at 65° C. The solution was then left to slowly evaporate at room temperature for two days. Colourless plate-like crystals were obtained within two days.

Each lithium cation exhibits tetrahedral coordination and bridged by four carboxylate moieties (from two L-prolines and two 3-methoxybenzoate anions) to form square grids.

Figure 6A:
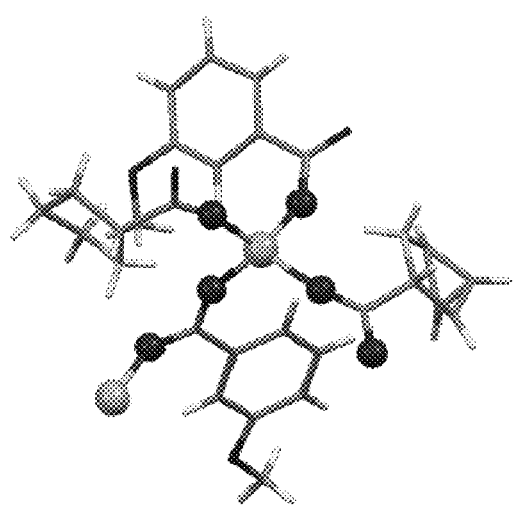
FIGS. 6A and 6B show the asymmetric unit and crystal packing of the material prepared in Example 6, respectively, according to embodiments of the present disclosure.
Figure 6B:
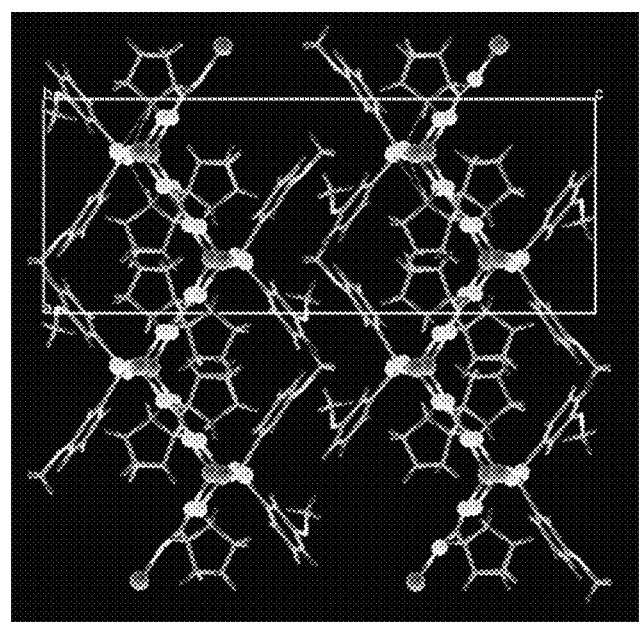

The crystal form is an anhydrous coordination polymer and the asymmetric unit and crystal packing are shown in FIGS. 6A and 6B.

EXAMPLE 7—PREPARATION OF [LI$_6$(SUCCINATE)$_3$(ISONICOTINAMIDE)$_6$]$_N$ (7)

Method 1: Single crystal: 210 mg (1.62 mmol) of lithium succinate (previously synthesized from grinding 406 mg (17.0 mmol) of lithium hydroxide with $1.01 \times 10^3$ mg (8.53 mmol) of succinic acid with 500 µL of water by hand for ~10 min. then left to dry overnight) and 33.0 mg (0.270 mmol) of isonicotinamide were sonicated in a warm bath until dissolved in ca. 0.7 mL of water. The solution was kept at room temperature and allowed to evaporate. Single crystals grew within four days.

Method 2: Grinding: 96.0 mg (4.01 mmol) of lithium hydroxide, 237 mg (2.01 mmol) of succinic acid and 489 mg (4.01 mmol) of isonicotinamide were ground together with 900 microL of DI H2O. The wet mass was ground in a mortar and pestle until dry. To facilitate drying of the solid, the mortar was placed on a warm hotplate until the solid was almost dry.

Lithium is tetrahedrally coordinated to succinate anions and isonicotinamide molecules. Lithium coordinated to succinate generates 6-membered lithium-carboxylate rings. The lithium-carboxylate rings connect to form chains. These chains are linked by succinate to form sheets. The nitrogen of isonicotinamide also coordinates to lithium and extends perpendicular to the sheet resulting in interdigitation of isonicotinamides of neighboring sheets. In the structure solved at 100K there are three independent isonicotinamide molecules in the asymmetric unit, however, in the structure solved at 273K there is only one isonicotinamide in the asymmetric unit.

EXAMPLE 8—PREPARATION OF LI(ADENINATE)(WATER)$_3$ (8)—COMPARATIVE

Lithium hydroxide (70.9 mg, 2.96 mmol) and adenine (200 mg, 1.48 mmol) were dissolved in ca. 2 mL of a 50:50 mixture of deionised water and ethanol. The solution was left to sonicate for 1 hour at 65° C. The clear solution was then left to slowly evaporate at room temperature. Yellow block-like crystals were obtained overnight.

The lithium cation coordinates to nitrogen on the purine ring and to three oxygens from neighbouring water molecules achieving tetrahedral coordination. The coordination of three water molecules to the lithium limits the ability for lithium to generate a coordination network and thus produces a discrete compound. The discrete compound, consisting of one adeninate, one lithium cation and three waters, interacts with adjacent compounds through O•••N hydrogen bonds. Neighbouring compounds propagate along a 21 screw parallel to the b-axis.

EXAMPLE 9—PREPARATION OF [LI(NICOTINATE)(SARCOSINE)(WATER)]$_N$ (9)—COMPARATIVE

Lithium hydroxide (47.9 mg, 2.00 mmol), nicotinic acid (98% pure, used as received from Aldrich, 246 mg, 2.00 mmol) and sarcosine (98% pure, used as received from Aldrich, 275 mg, 3.09 mmol) were dissolved in ca. 3 mL of deionised water. It was maintained on the hot plate until crystals emerged from the hot solution. Colorless needles were collected from the hot solution and used for further analysis.

The resultant crystals were characterized by single crystal X-ray crystallography. Each lithium cation is bridged by carboxylates of sarcosine molecules to form 1D chain. The tetrahedral coordination of lithium cation is achieved by coordination of two carboxylates from sarcosine, one carboxylate of nicotinate and one water molecule.

EXAMPLE 10—PREPARATION OF [LI(PYRIDOXINATE)(WATER)]$^N$ (10)—COMPARATIVE

Lithium hydroxide (240 mg, 10.0 mol) and pyridoxine ($1.69 \times 10^3$ mg, 9.99 mol) were dissolved in 4 mL of deionised water and placed on a hotplate until crystals emerged from the hot solution. Colorless needles were harvested from the hot solution and used for further analysis.

Crystals of [Li(pyridoxinate)(water)]$_n$ were characterized by single crystal X-ray crystallography, powder X-ray diffraction and TGA.

Each lithium cation is coordinated to one deprotonated hydroxyl group, two hydroxyl groups (from two different pyridoxinates) and one water molecule to achieve tetrahedral coordination. The pyridoxinates thus bridge the lithium cations through the lithium-hydroxyl interactions, generating a chain along the crystallographic c-axis. The chains are connected through water-pyridoxinate O—H . . . N hydrogen bonds, forming a hydrogen bonded sheet.

EXAMPLE 11—PREPARATION OF [(IMIDAZOLIUM)$_2$$^+$(LI(HYDROGEN OXALATE)(OXALATE))$^-$(OXALIC ACID)]

13.0 mg, 543 mmol of lithium hydroxide, 94.0 mg, 1.04 mmol of oxalic acid and 36.0 mg, 529 mmol of imidazole were dissolved in ca.1 mL of water. The solution was kept at room temperature and allowed to evaporate until single crystals suitable for X-ray diffraction were obtained.

Each lithium cation is coordinated to one hydrogen oxalate anion and one oxalate dianion generating a complex anion. Two complex anions are connected by lithium-oxygen coordination bonds supporting square pyramidal coordination of lithium. Imidazole cations are present in the lattice, balancing the charge and interacting with the complex anion through N—H . . . O charge assisted hydrogen bonds. The crystal lattice also contains oxalic acid which interacts with the complex anion through O—H . . . O hydrogen bonds.

EXAMPLE 12

Further crystalline samples of 11-33 were prepared and characterised using methods analogous to these described above in examples 1 to 11.

The stability of these compounds under warm humid conditions was assessed as follows:

The crystalline material was stored at 40° C. in an atmosphere of 75% relative humidity.

The results are shown in table 1.

TABLE 1

| Compound | Aqua complex, hydrate or anhydrous | Lithium incorporated as | Stable? |
|---|---|---|---|
| 1 [Li(2-methoxybenzoate)(L-proline)]$_n$ | Anhydrous | Coordination polymer | Yes |
| 2 [Li$_2$(fumarate)(isonicotinamide)$_2$]$_n$ | Anhydrous | Coordination polymer | Yes |
| 3 [Li(4-hydroxybenzoate)]$_n$ | Anhydrous | Coordination polymer | Yes |
| 4 [Li(4-methoxybenzoate)]$_n$ | Anhydrous | Coordination polymer | Yes |
| 5 [Li(4-methoxybenzoate)(L-proline)]$_n$ | Anhydrous | Coordination polymer | Yes |
| 6 [Li(3-methoxybenzoate)(L-proline)]$_n$ | Anhydrous | Coordination polymer | Yes |
| 7 [Li$_2$(succinate) (isonicotinamide)$_2$]$_n$ | Anhydrous | Coordination polymer | Yes |
| 8 Li(adeninate)(water)$_3$ | Aqua complex | Molecular complex | No |
| 9 [Li(nicotinate)(sarcosine)(water)]$_n$ | Aqua complex | Coordination polymer | No |
| 10 [Li(pyridoxinate)(water)]$_n$ | Aqua complex | Coordination polymer | No |
| 11 [(imidazolium)$_2$$^+$(Li(hydrogen oxalate)(oxalate))$^-$(oxalic acid)] | Anhydrous | Complex anion | No |
| 12 [Li(benzoate)(L-proline)]$_n$ | Anhydrous | Coordination polymer | Yes |
| 13 [Li(salicylate)(4-hydroxyproline)]$_n$ | Anhydrous | Coordination polymer | Yes |
| 14 [Li(salicylate)(L-proline)]$_n$ | Anhydrous | Coordination polymer | Yes |
| 15 [Li$_2$ (fumarate)]$_n$ | Anhydrous | Coordination polymer | Yes |
| 16 [Li$_2$ (succinate)]$_n$ | Anhydrous | Coordination polymer | Yes |
| 17 [Li$_2$ (oxalate)]$_n$ | Anhydrous | Coordination polymer | Yes |
| 18 [Li (benzoate)]$_n$ | Anhydrous | Coordination polymer | Yes |
| 19 [Li(sarcosine)(4-hydroxybenzoate)(water)]$_n$ | Aqua complex | Coordination polymer | No |
| 20 [Li$_2$(tartrate)(L-proline)(water)$_2$]$_n$ | Aqua complex | Coordination polymer | No |
| 21 [(Li$_2$(lactate)$_2$(water)$_2$)(urea)]$_n$ | Aqua complex | Coordination polymer | No |
| 22 [Li(maleate)(isonicotinamide) (water)]$_n$ | Aqua complex | Coordination polymer | No |
| 23 [Li(acesulfame)(water)]$_n$ | Aqua complex | Coordination polymer | No |
| 24 [Li$_4$(salicylate)$_2$(water)$_2$]$_n$ | Aqua complex | Coordination polymer | No |
| 25 [Li$_2$(oxalate)(beta-alanine)$_2$(water)]$_n$ | Aqua complex | Coordination polymer | No |
| 26 {[Li(malate) (water)$_2$]•(imidazolium)}$_n$ | Aqua complex | Coordination polymer | No |
| 27 [Li(hydrogen maleate)(sarcosine)(water)] | Aqua complex | Molecular complex | No |
| 28 [Li$_2$(camphorsulphonate)$_2$(urea)$_2$ (water)$_2$] | Aqua complex | Molecular complex | No |
| 29 [Li(camphorsulfonate)(water)$_2$] | Aqua complex | Molecular complex | No |
| 30 [Li(camphorsulfonate)(sarcosine)(water)$_2$] | Aqua complex | Molecular complex | No |
| 31 {[Li(p-toluenesulfonate)]•H30}$_n$ | H$_5$O$_2$ Hydrate | Molecular complex | No |
| 32 [Li$_2$(salicylate)$_2$(isonicotinamide)$_4$]$_2$ | Anhydrous | Molecular complex | No |
| 33 [(imidazolium)$_2$$^+$(Li(hydrogen malate)$_2$(water))$^-$] | Aqua complex | Complex anion | No |
| 34 [(Li(camphorsulfonate)(L-proline))$_2$](water)]$_n$ | Hydrate | Coordination polymer | No |

Compounds were classed as stable if they retained their crystal form for at least two weeks as verified by examination of PXRD patterns collected before and after exposure to humidity.

Figure 7A:
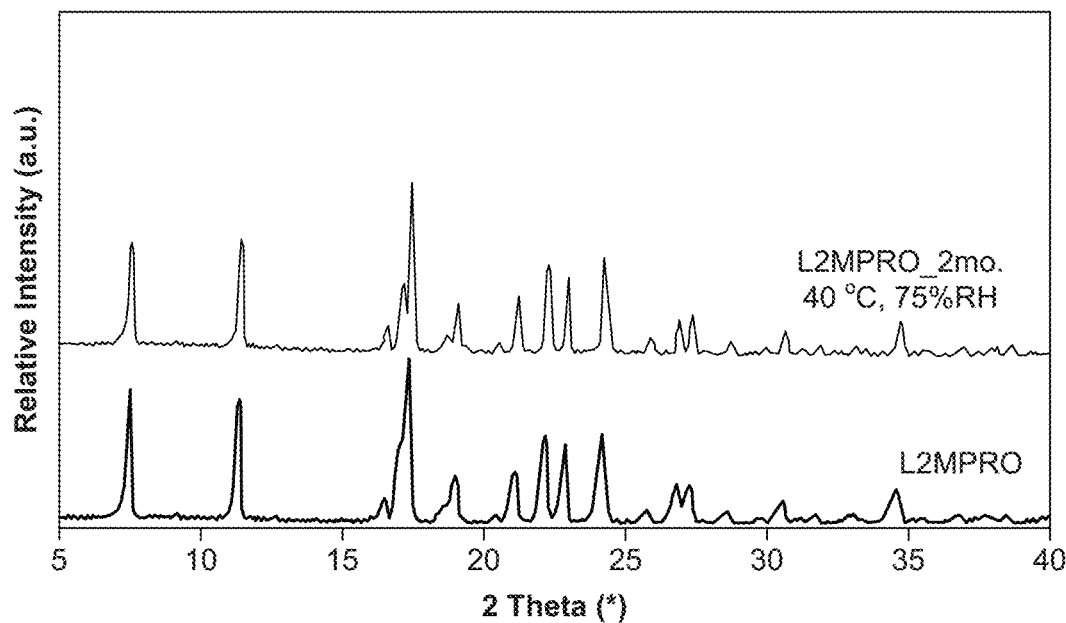
FIG. 7A shows the initial PXRD pattern of compound 1 (lower trace) and the PXRD pattern after 2 months at 75% relative humidity and 40° C. (upper trace) of compound 1, according to embodiments of the present disclosure.

For example, FIG. 7A shows the initial PXRD pattern of compound 1 (of the invention, lower trace) and the pattern after 2 months at 75% relative humidity and 40° C. (upper trace). These appear substantially identical.

Figure 7B:
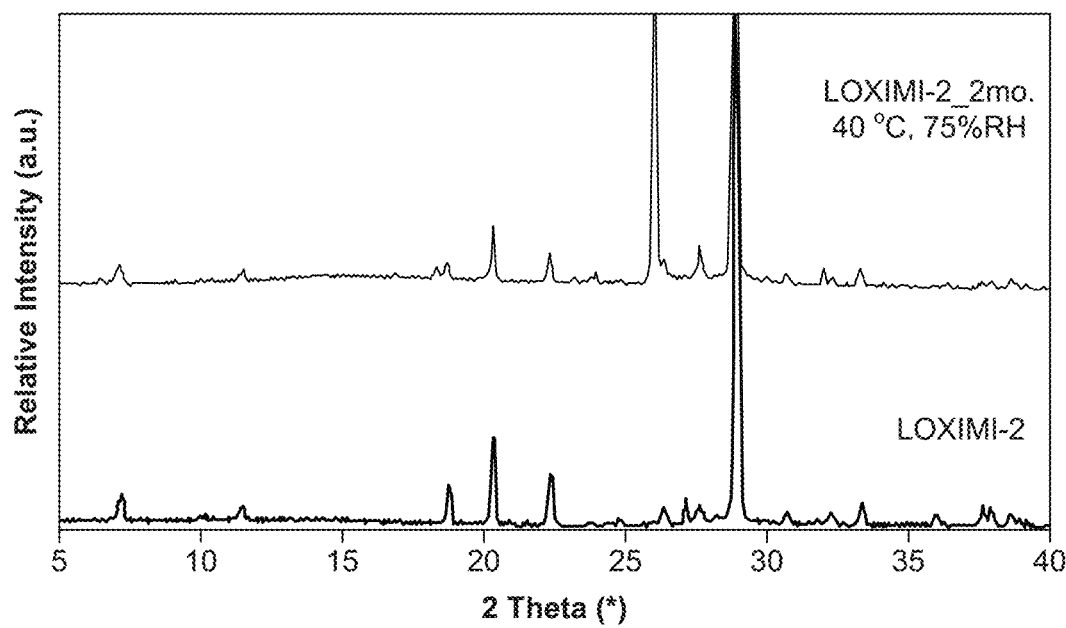
FIG. 7B shows the initial PXRD pattern of compound 11 (lower trace) and the PXRD pattern after 2 months at 75% relative humidity and 40° C. (upper trace) of compound 11, according to embodiments of the present disclosure.

FIG. 7B shows the initial pattern of compound 11 (comparative, initial spectrum lower trace). It can be seen that the pattern obtained after 2 months at 75% relative humidity and 40° C. (upper trace) in this case is different.

Figure 8:
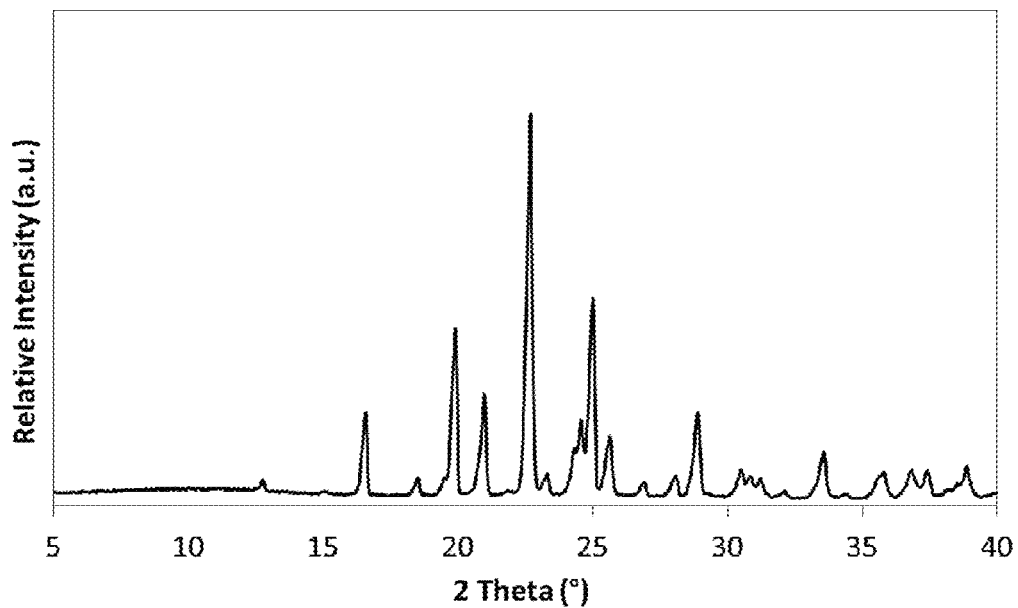
FIG. 8 shows the PXRD pattern of compound 2, according to embodiments of the present disclosure.
Figure 9:
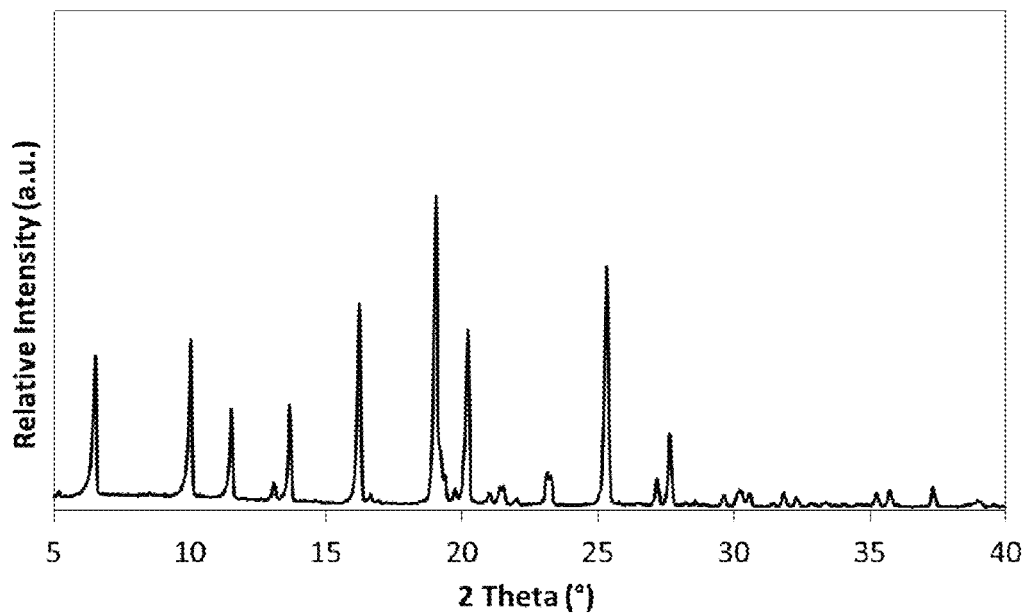
FIG. 9 shows the PXRD pattern of compound 5, according to embodiments of the present disclosure.
Figure 10:
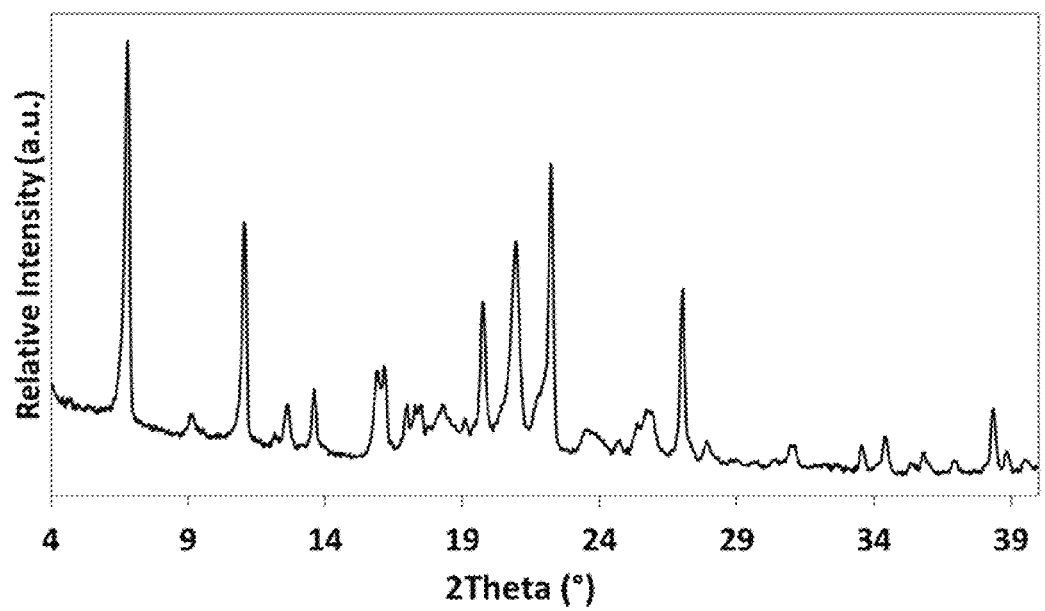
FIG. 10 shows the PXRD pattern of compound 6, according to embodiments of the present disclosure.
Figure 11:
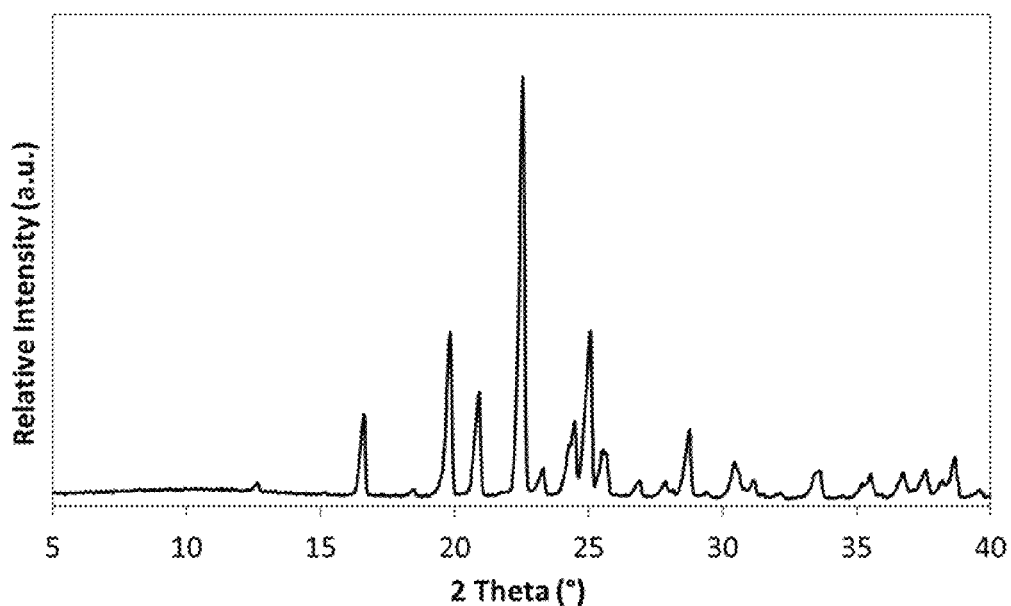
FIG. 11 shows the PXRD pattern of compound 7, according to embodiments of the present disclosure.

FIG. 8 shows the PXRD pattern of compound 2; FIG. 9 shows the PXRD pattern of compound 5; FIG. 10 shows the PXRD pattern of compound 6; and FIG. 11 shows the PXRD pattern of compound 7.

EXAMPLE 13

The bioavailability of the compounds prepared in examples 1 to 7 was measured using in vivo studies in rats.

Male Sprague-Dawley rats, weighing 240-290 g, were treated through gastric intubation with formulations of lithium and compared with lithium carbonate as a reference. For each formulation a group of 12 rats was treated. 4 mEq/kg of lithium were orally administered, after suspension in 2 mL of corn seeds oil ("Olio Cuore").

Four intervals' post-administration time (2, 24, 48 and 72 hours) were considered and three rats for each of them, employing the protocol used by Zaworotko and coworkers (Smith et al., Mol. Pharmaceutics 2013, 10, 4728-4738). At each time interval blood samples were collected through intra-cardiac injection, these were treated with 50 μL of sodium heparin and centrifuged for 10 min at 1600 rpm. Plasma samples of approximately 5 mL each were thus obtained. The brain was explanted in toto with perfusion with phosphate buffered saline (PBS) in order to preserve it in a viable state. The plasma and brain samples were immediately frozen at a temperature of −80° C., after measuring the weight of the brains.

Sample Preparation Before ICP-OES Analysis

In order to determine the concentration of the lithium by means of the ICP-OES (Inductively Coupled Plasma Optical Emission Spectometry) analysis, plasma and brain samples were purified and mineralized, respectively to obtain solutions suitable for analysis.

Plasma Purification

A 0.5 mL aliquot was taken from each sample, to which were added equal amounts of MilliQ water and concentrated nitric acid, in order to bring the lithium ion in solution in the form of $LiNO_3$ and to obtain the precipitation of the proteins. At this point, each sample was sonicated for 10 min in an ultrasonic bath and diluted to a volume of 5.0 mL.

All samples were subjected to centrifugation for a period of 40 min, at a rotational speed of 6000 rpm, to obtain complete plasma proteins/solution separation. At the end supernatant liquid containing lithium was diluted to a final volume of 15 mL by adding MilliQ water. The obtained solutions were stored at a temperature of 4° C. until analysis.

Mineralization of Brain Samples

The purpose of this phase was to obtain liquid samples, suitable to ICP-OES analysis, containing lithium in solution, starting from the solid organic tissue of the brain. The mineralization process allows the complete degradation of organic substances until the total transformation into simple inorganic substances.

The first operation performed was that the drying of the fabric, obtained through the use of a digester open PerkinElmer SPB 100-12: each sample of brain has been inserted in special containers Digitube™ 100 mL and maintained at a temperature of 80° C. for 120 min.

The second step involved the mineralization true and proper brain: each sample were added to 10 mL of concentrated nitric acid and 1.0 mL of hydrogen peroxide, then the system was brought to a temperature of 120° C. for 120 min. until the complete mineralization. With this procedure you get the desired biological degradation of organic compounds and the consequent passage of lithium in solution. The solutions thus obtained were collected, brought to a final volume of 20 mL with MilliQ water and preserved at a temperature of 4° C. until time of analysis.

Quantitative Analysis

In order to obtain the determination of lithium ion concentrations in the samples previously prepared, optical emission spectrometry inductively coupled plasma ICP-OES was used (PerkinElmer Optima 8000 spectrometer).

The analysis was conducted at the fixed wavelength of lithium ($\lambda$=670.784 nm) and the intensity of the radiation emitted by each sample was measured and compared standard solutions.

Plasma and brain concentration data were processed using a non-compartmental approach using WinNonlin® software (Pharsight Corporation, USA) and Microsoft Excel XP (Microsoft Corporation, Palo Alto, CA 94306 USA).

This way the following parameters has been obtained in both compartments:

$t_{max}$ (h): time (after the administration) of $C_{max}$ detection;
$C_{max}$: highest concentration value;
AUC last: area under the concentration vs time curve (expressed as mg*h/mL or mg*h/g in plasma and brain, respectively), calculated from time 0 to the last quantifiable point, according to the log-linear trapezoidal method (linear up to $C_{max}$, logarithmic after $C_{max}$);
t½ (h): half-life time of the disappearance of the terminal phase, otherwise known as t½_Lambda_z.
Last MRT (h): mean residence time in the compartment.

The results obtained by ICP-OES analysis of the solutions obtained from the purification of plasma samples and brain mineralization are shown in Table 2.

Figure 12:
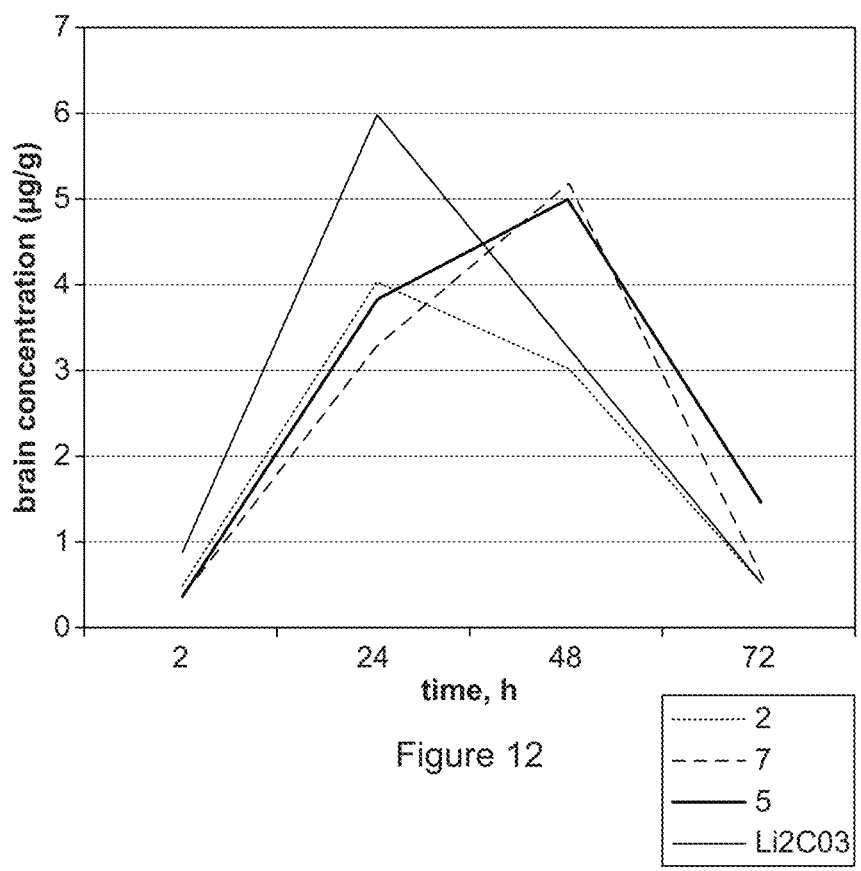
FIG. 12 shows a plot of the lithium concentration in the brain vs. time for compounds 2, 5, 7, and lithium carbonate, respectively, according to embodiments of the present disclosure.

FIG. 12 illustrates how for compounds 2, 5 and 7, a higher concentration of lithium in the brain is achieved after 48 hours, compared with the use of lithium carbonate.

Table 2

| Example | PLASMA CONC(μg/ml) Time(h) | | | | BRAIN CONC. (μg/g) Time(h) | | | |
|---|---|---|---|---|---|---|---|---|
| | 2.00 | 24.00 | 48.00 | 72.00 | 2.00 | 24.00 | 48.00 | 72.00 |
| 2 | 3.09 | 4.22 | 0.55 | 0.35 | 0.50 | 4.59 | 1.96 | 0.55 |
| | 1.59 | 3.29 | 1.16 | 0.38 | 0.32 | 2.66 | 3.35 | 0.52 |
| | 2.02 | 4.42 | 1.31 | 0.39 | 0.68 | 4.81 | 3.74 | 0.59 |
| 7 | 0.80 | 3.84 | 2.52 | 0.51 | 0.42 | 3.69 | 3.67 | 0.79 |
| | 1.78 | 4.91 | 3.01 | 0.48 | 0.36 | 3.69 | 6.05 | 0.56 |
| | 3.46 | 3.67 | 3.44 | 0.37 | 0.66 | 2.40 | 5.74 | 0.48 |
| 5 | 2.82 | 7.15 | 1.45 | 0.63 | 0.23 | 4.44 | 4.42 | 1.08 |
| | 4.02 | 6.80 | 1.91 | 0.48 | 0.48 | 4.46 | 4.76 | 0.43 |
| | 2.65 | 4.29 | 3.65 | 1.32 | 0.46 | 2.54 | 5.77 | 2.84 |
| 3 | 4.40 | 4.78 | 1.20 | 0.39 | 0.83 | 2.01 | 3.45 | 0.52 |
| | 1.88 | 5.05 | 0.95 | 0.30 | 0.55 | 4.12 | 3.27 | 0.87 |
| | 0.34 | 8.63 | 1.50 | 0.23 | 0.30 | 6.20 | 3.74 | 0.80 |
| 4 | 3.10 | 3.99 | 0.94 | 0.46 | 0.88 | 4.21 | 2.82 | 0.94 |
| | 1.91 | 8.35 | 1.19 | 0.21 | 0.45 | 5.70 | 3.34 | 0.66 |
| | 2.01 | 7.15 | 3.27 | 0.27 | 0.58 | 4.40 | 6.14 | 0.73 |
| 1 | 3.43 | 3.85 | 0.97 | 0.23 | 0.96 | 3.64 | 2.81 | 0.62 |
| | 1.78 | 6.01 | 1.78 | 0.40 | 0.71 | 4.28 | 4.50 | 0.68 |
| | 2.31 | 2.50 | 0.85 | 0.31 | 0.68 | 2.60 | 2.06 | 0.51 |
| 6 | 3.03 | 5.95 | 0.67 | 0.23 | 0.64 | 4.54 | 2.84 | 0.59 |
| | 1.43 | 4.76 | 0.74 | 0.31 | 0.44 | 4.21 | 2.06 | 0.49 |
| | 3.38 | 8.44 | 0.87 | 0.25 | 0.73 | 4.37 | 2.46 | 0.43 |
| Lithium carbonate | 3.02 | 8.72 | 1.29 | 0.14 | 0.60 | 7.89 | 3.35 | 0.54 |
| | 4.82 | 5.32 | 1.18 | 0.06 | 1.43 | 4.55 | 2.89 | 0.52 |
| | 2.72 | 11.20 | 1.60 | 0.08 | 0.68 | 5.53 | 3.43 | 0.55 |

In the next step of the research, the profiles in both plasma and brain compartments were analyzed by non-compartmental model using WinonLin® software. Relative bioavailability was then calculated as compared to lithium carbonate. Finally the ratio of bioavailability in the blood compared with the brain was calculated. The results are shown in table 3 below:

TABLE 3

| Example | Tmax | Cmax | AUClast | t½_Lambda_z | Relative Plasma BA (UL crystal forms, oral vs Li2CO3 oral)(%) | Tmax | Cmax | AUClast | t½_Lambda_z | Relative Brain BA (UL crystal forms, oral vs Li2CO3, oral) (%) | AUC (Cerebral)/ AUC (Plasma) |
|---|---|---|---|---|---|---|---|---|---|---|---|
| | 24 | 8.4133 | 269.4267 | 7.3913 | 100.00 | 24 | 5.9900 | 232.4100 | 13.7913 | 100.00 | 0.863 |
| 1 | 24 | 4.1200 | 157.4000 | 12.9141 | 58.42 | 24 | 3.5067 | 172.2533 | 18.9045 | 74.12 | 1.094 |
| 2 | 24 | 3.9767 | 146.9033 | 14.0638 | 54.52 | 24 | 4.0200 | 177.5000 | 16.7775 | 76.37 | 1.208 |
| 3 | 24 | 6.1533 | 200.8867 | 11.0941 | 74.56 | 24 | 4.1100 | 193.6900 | 19.2526 | 83.34 | 0.964 |
| 4 | 24 | 6.4967 | 224.4633 | 10.9741 | 83.31 | 24 | 4.7700 | 225.0700 | 18.3303 | 96.84 | 1.003 |

TABLE 3-continued

| Example | Tmax | Cmax | AUClast | t½_Lambda_z | Relative Plasma BA (UL crystal forms, oral vs Li2CO3 oral)(%) | Tmax | Cmax | AUClast | t½_Lambda_z | Relative Brain BA (UL crystal forms, oral vs Li2CO3, oral) (%) | AUC (Cerebral)/ AUC (Plasma) |
|---|---|---|---|---|---|---|---|---|---|---|---|
| 5 | 24 | 6.0800 | 243.6000 | 16.5057 | 90.41 | 48 | 4.9833 | 229.3867 | 13.4751 | 98.70 | 0.942 |
| 6 | 24 | 6.3833 | 199.5767 | 10.4363 | 74.07 | 24 | 4.3733 | 172.7467 | 15.3888 | 74.33 | 0.855 |
| 7 | 24 | 4.1400 | 196.5800 | 15.0424 | 72.96 | 48 | 5.1533 | 211.7400 | 7.7957 | 91.11 | 1.077 |

What is claimed is:

1. A compound comprising:

lithium ions, the conjugate base of an acid selected from the group consisting of: fumaric acid and succinic acid, and isonicotinamide.

2. The compound of claim 1, wherein the compound is selected from the group consisting of:

(a) a compound comprising lithium cations, fumarate anions and isonicotinamide molecules, in a molar ratio of 2:1:2; and (b) a compound comprising lithium cations, succinate anions and isonicotinamide molecules, in a molar ratio of 2:1:2.

3. A pharmaceutical composition comprising the compound of claim 1.

4. A pharmaceutical composition comprising the compound of claim 2.

5. The compound of claim 1, which exhibits a lower maximum lithium concentration in blood plasma ($C_{max}$) and a later time of maximum concentration in the brain ($T_{max}$) after a single oral dose compared with an equivalent single oral dose of lithium carbonate.

* * * * *